United States Patent [19]

Heimer

[11] Patent Number: 4,712,179
[45] Date of Patent: Dec. 8, 1987

[54] METHOD AND APPARATUS FOR CALIBRATING INTERNAL MEASUREMENTS OF AN IMPLANTED CARDIAC PACER

[75] Inventor: Malcolm L. Heimer, Miami, Fla.

[73] Assignee: Cordis Corporation, Miami, Fla.

[21] Appl. No.: 15,492

[22] Filed: Feb. 5, 1987

Related U.S. Application Data

[63] Continuation of Ser. No. 641,186, Aug. 15, 1984, abandoned.

[51] Int. Cl.$^4$ .......................... G06F 15/42; A61N 1/36
[52] U.S. Cl. ............................. 364/417; 128/419 PT; 128/903; 364/571
[58] Field of Search .................. 128/419 PT, 419 PG, 128/903 P, 417, 413; 364/417, 571; 331/65

[56] References Cited

U.S. PATENT DOCUMENTS

| | | | |
|---|---|---|---|
| 3,766,908 | 10/1973 | Haynes | 128/73 L |
| 4,142,533 | 3/1979 | Brownlee | 128/419 PT |
| 4,324,251 | 4/1982 | Mann | 128/419 PT |
| 4,332,256 | 6/1982 | Brownlee | 128/419 PT |
| 4,335,371 | 6/1982 | Connolly | 364/571 |
| 4,418,392 | 11/1983 | Hata | 364/571 |
| 4,446,715 | 5/1984 | Bailey | 364/571 |
| 4,522,208 | 6/1985 | Buffet | 128/419 PT |
| 4,550,370 | 10/1985 | Baker | 128/417 |
| 4,562,841 | 1/1986 | Brockway | 128/419 PG |

Primary Examiner—Jerry Smith
Assistant Examiner—Gail Hayes
Attorney, Agent, or Firm—George H. Gerstman

[57] ABSTRACT

An implantable cardiac pacer having pacer circuitry for producing output stimulation pulses on leads connectable to a patient's heart includes internal measurement circuitry for producing uncorrected measurement values relative to battery conditions and to pulses from the pacing circuitry. The pacer has a data processing unit with a microprocessor and a RAM device for storing, in dedicated locations, programmed gain and offset correction factors for the uncorrected measurement values. Telemetry means is responsive to the microprocessor for transmitting the uncorrected measurement values and the correction factors to an external programmer/receiver unit. The programmer/receiver unit includes telemetry means for receiving the uncorrected measurement values and the correction factors from the pacer. The programmer/receiver unit further includes a data processing device having an ROM device for storing an algorithm and a microprocessor for calculating corrected measurement values from the uncorrected measurement values and the correction factors.

6 Claims, 4 Drawing Figures

METHOD AND APPARATUS FOR CALIBRATING INTERNAL MEASUREMENTS OF AN IMPLANTED CARDIAC PACER

This application is a continuation of U.S. application Ser. No. 641,186, filed Aug. 15, 1984, and now abandoned.

BACKGROUND OF THE INVENTION

This invention relates generally to an implanted cardiac pacer and more particularly, it relates to a method and apparatus for calibrating internal measurements of an implanted cardiac pacer by "software trims".

Heretofore, when resistive components are required to be used in conjunction with hybrid integrated circuits, external resistor elements were connected by external wires to the integrated circuits. In order to overcome this disadvantage, resistive values have been plated directly to the ceramic substrate during the manufacturing of the hybrid integrated circuits. The plated material is generally in the form of a hardened resistive ink. Since these plated resistors on the hybrid integrated circuit are required to be of a precise value, they are checked in the manufacturing process and then are trimmed mechanically to the desired value if they are found to be inaccurate. Typically, this is achieved by the use of a laser beam or other mechanical means for removing a portion of the plated resistive material.

It would therefore be desirable to provide means for avoiding the necessity of mechanically trimming the resistors on the hybrid integrated circuits after manufacturing. The present invention provides a means for calibrating internal measurements of an implanted cardiac pacer by using a series of calibration measurements which are performed during the manufacturing process. Specifically, these internal measurement results are compared to the correct values obtained from a precise external instrument and correction factors are computed. The correction factors are then programmed into the pacer to be stored in a dedicated random-access memory (RAM) device. When an external programmer/receiver commands via telemetry the reading of the uncorrected or raw internal measurements, there will be telemetered from the implanted pacer these internal measurements accompanied along with correction factors for each respective measurement. The programmer/receiver includes a read-only memory (ROM) for storing an algorithm programmed therein and a microprocessor for computing corrected measurement values for visual display.

SUMMARY OF THE INVENTION

Accordingly, it is a general object of the present invention to provide an improved cardiac pacer which includes means for calibrating internal measurements thereof.

It is an object of the present invention to provide an implantable cardiac pacer which includes internal measuring means for producing uncorrected measurement values and a memory device for storing programmed correction factors therefor.

It is another object of the present invention to provide an implantable cardiac pacere which includes telemetry means responsive to a microprocessor for transmitting uncorrected measurements signals and correction factor signals for each of the uncorrected measurement signals to an external programmer/receiver unit.

It is still another object of the present invention to provide a cardiac pacer system which includes a programmer/receiver unit having a read-only memory for storing an algorithm and a microprocessor for calculating corrected measurement values for display from uncorrected internal measurements and corresponding correction factors telemetered by an implantable cardiac pacer.

In accordance with these aims and objectives, the present invention is concerned with the provision of an implantable cardiac pacer having pacing circuitry for producing output stimulation pulses on leads connectable to the patient's heart which includes internal measuring means for producing uncorrected measurement values relative to battery conditions and to pulses from the pacing circuitry. The cardiac pacer includes a data processing unit having a microprocessor and a random-access memory device for storing, in dedicated locations, a programmed gain and offset correction factors for the uncorrected measurement values. Telemetry means is responsive to the microprocessor for transmitting the uncorrected measurement signals and the correction factors for each of the uncorrected measurement signals to an external programmer/receiver unit.

In another aspect of the present invention, there is provided a cardiac pacing system which includes a programmer/receiver unit having a read-only memory device for storing an algorithm and a microprocessor for calculating corrected measurement values from uncorrected measurements and correction factors telemetered from an implantable cardiac pacer for visual display.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 1:
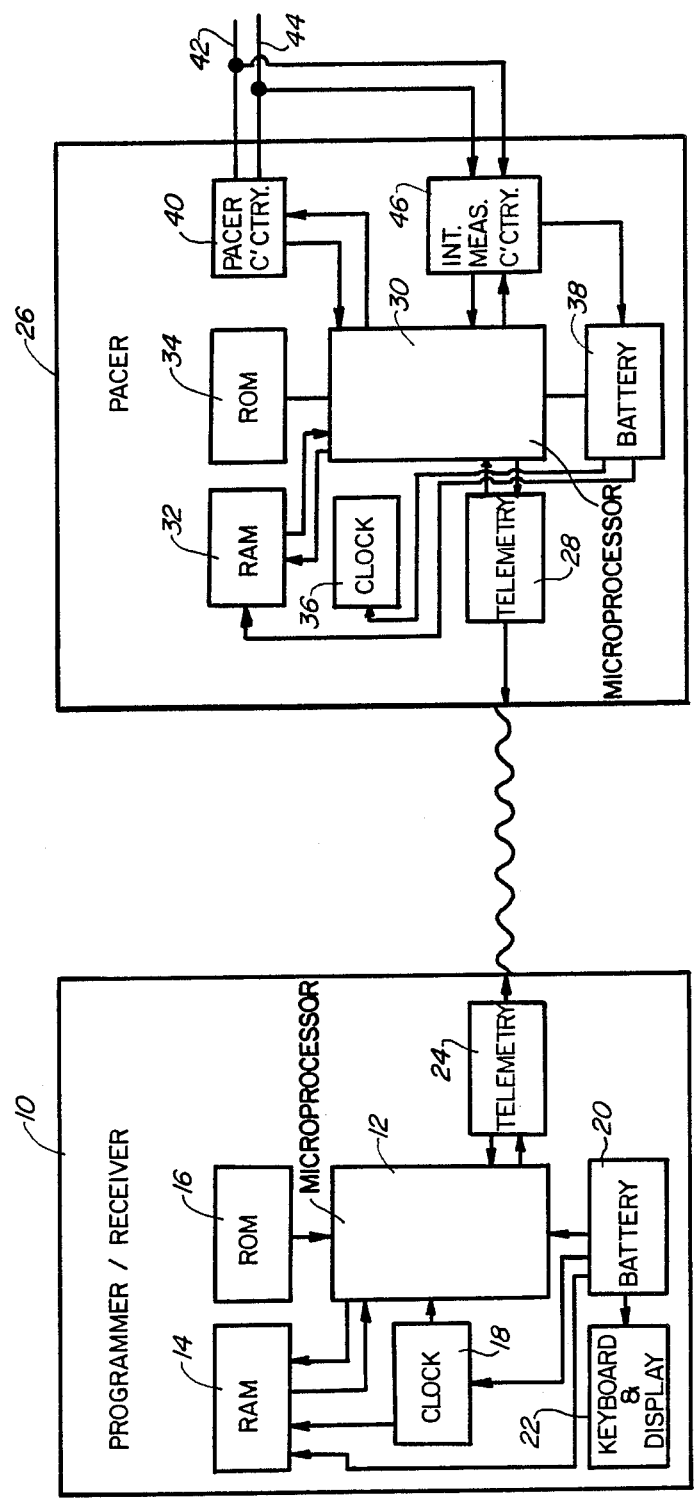
FIG. 1 is a functional block diagram of the overall cardiac pacer system embodying the principles of the present invention.

Referring now in detail to the various views of the drawings, there is shown in FIG. 1, in block diagram form, an overall cardiac pacing system consisting of an external programmer/receiver unit and an implantable cardiac pacer embodying the principles of the present invention. The external programmer/receiver unit 10 includes a data processing unit formed of a microprocessor 12 with associated random-access memory device (RAM) 14 and a read-only memory device (ROM) 16. The microprocessor is perferably a single chip CMOS 8-bit type such as RCA CDP 1802. The timing for all operations in the microprocessor 12 is controlled by a clock 18. A battery 20 is a self-contained power supply for driving all of the electric circuitry in the programmer/receiver unit. A combination keyboard and display unit 22 is utilized for parameter selection, review and programming by an operator and for displaying visually a particular result commanded by the operator. A telemetry unit 24 is provided for two-way communication with a cardiac pacer 26 which is implanted in the body at a suitable location of a heart patient.

The pacer 26 has a telemetry unit 28 for receiving and transmitting data relative to the programmer/receiver unit 10 via the telemetry unit 24. The pacer 26 includes a microprocessor 30 with associated random-access memory device (RAM) 32 and read-only memory device (ROM) 34, which is of the same type as the respective microprocessor circuit 12, RAM 14, and ROM 16 in the programmer/receiver unit 10. A clock 36 is likewise provided for appropriately sequencing the microprocessor 30 through all of its operations, and a battery 38 is self-contained power supply for driving all the electronic circuitry in the pacer 26. Pacer circuitry 40 is provided for supplying output stimulation pulses on multi-conductor leads 42, 44. The substantial improvement of the present invention depends in part on the provision of an internal measuring circuitry 36 which calibrates the internal measurement values or results through the use of "software trims".

During the manufacturing process of the electronic components for the cardiac pacer which are implemented on hybrid integrated circuits, there are required the use of plated resistors that must be precisely calibrated. As previously mentioned, the prior art utilized a mechanical trimming of the resistors. In order to avoid the need of such mechanical trimming, a series of calibration measurements are performed on the pacer unit of the instant invention after the manufacturing process. These measurement results are compared to correct values obtained from an external precision measurement circuitry and correction factors are computed. These correction factors are then programmed into the pacer 26 to be stored in dedicated locations of RAM 32. The telemetry of a particular measurement result will be accompanied by certain correction factors for that measurement. An algorithm programmed in the ROM 16 of the programmer/receiver unit 10 will compute via the microprocessor 12 the corrected measurement value for visual indication on the display unit 22.

Figure 2:
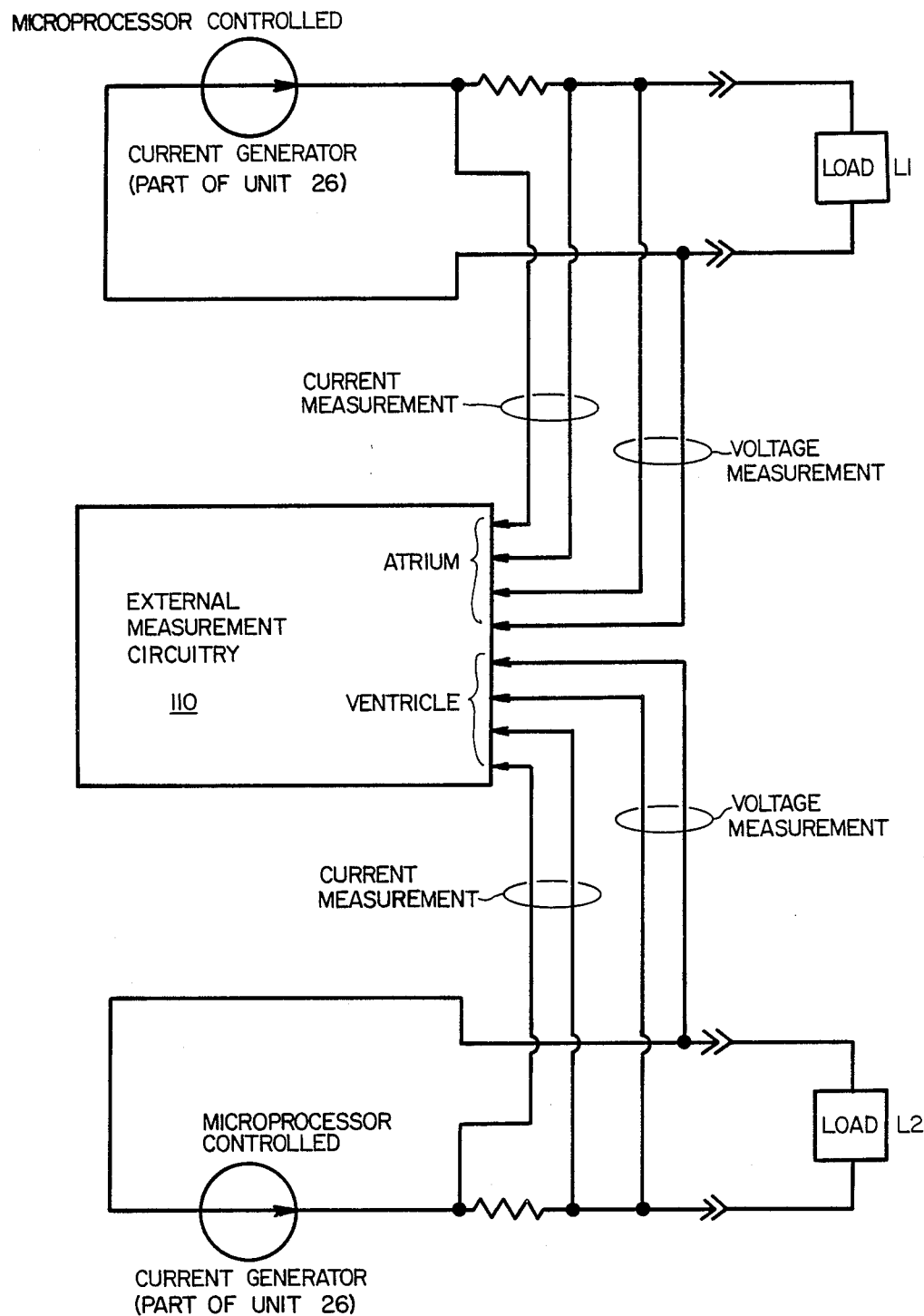
FIG. 2 illustrates schematically how the correction factors are determined by an external measurement circuitry.

After the pacer has been manufactured, the correction factors are determined and will now be explained in more detail by reference to FIG. 2 of the drawings. Two correction factors for each pulse voltage and pulse current measurements in the atrium will be determined. This is shown in the upper portion of FIG. 2. The correction factors consist of a gain factor and an offset factor. Similarly, two correction factors are determined for each pulse voltage and pulse current measurements in the ventricle. This is depicted in the lower portion of FIG. 2. Since the procedure for obtaining the correction factors for the atrium and the ventricle are identical, it will suffice to discuss only the atrium pulse voltage and pulse current measurements.

With respect to the pulse voltage measurements, a dummy load L1 representing the atrial heart chamber is connected to the leads of a completed pacer and the pacer will be programmed to generate a maximum current output pulse. A precision external measurement circuitry 110 of a conventional type well known in the art will be attached across the load L1 when the pacer is generating the maximum current output pulse so that an exact or correct pulse voltage can be externally measured. At the same time, the internal measurement circuitry 46 of the pacer 26 is simultaneously measuring the pulse voltage. The internal measurement is telemetered out and recorded. Then, the pacer will be programmed to generate a minimum current output and again the external measurement by the circuitry 110 will be made across the load L1. Likewise, an internal measurement will also be made. From these four measurements, the two correction factors consisting of the gain factor and the offset factor will be computed by comparing the differences between external measurements and the internal measurements. These correction factors will be stored in the appropriate locations in the RAM 32 of the pacer. Thereafter, both external and internal measurements will be made with respect to the pulse current and correction factors will be computed. The procedure is identical to that of the pulse voltage measurements except that the maximum and minimum currents will be the parameter being measured.

Whenever a particular measurement result is telemetered out by the telemetry unit 28, the data transmitted will consist of the uncorrected or raw internal measurement value, the gain correction factor, and the offset correction factor which is received by the programmer/receiver 10. The ROM 16 will have stored a correction algorithm according to the following equation:

$$M^1 = C(K_1 + K_2 M)$$

M = uncorrected measurement value
$K_2$ = gain correction factor
$K_1$ = offset correction factor
C = constant scaling factor
$M^1$ = corrected measurement value The microprocessor 12 will compute the corrected measurement value M' for display in the programmer/receiver 10. This algorithm is defined as the "software trim" which provides effective compensation for difference in values of the actual components used in the cardiac pacer. Thus, the mechanical trimming of the hybrid resistors has been eliminated during the manufacturing process. Further, more accurate results are obtained from the two correction factors than from trimming a single resistor. The constant scaling factor C is merely used to convert the binary results to a decimal format which is easier for the operator to understand.

In addition to the pulse voltage and pulse current measurements, there will also be made a battery terminal voltage measurement and a battery sensor measurement. Correction factors will also be computed for them and will be stored similarly in the RAM 32 of the pacer.

Figure 3A:
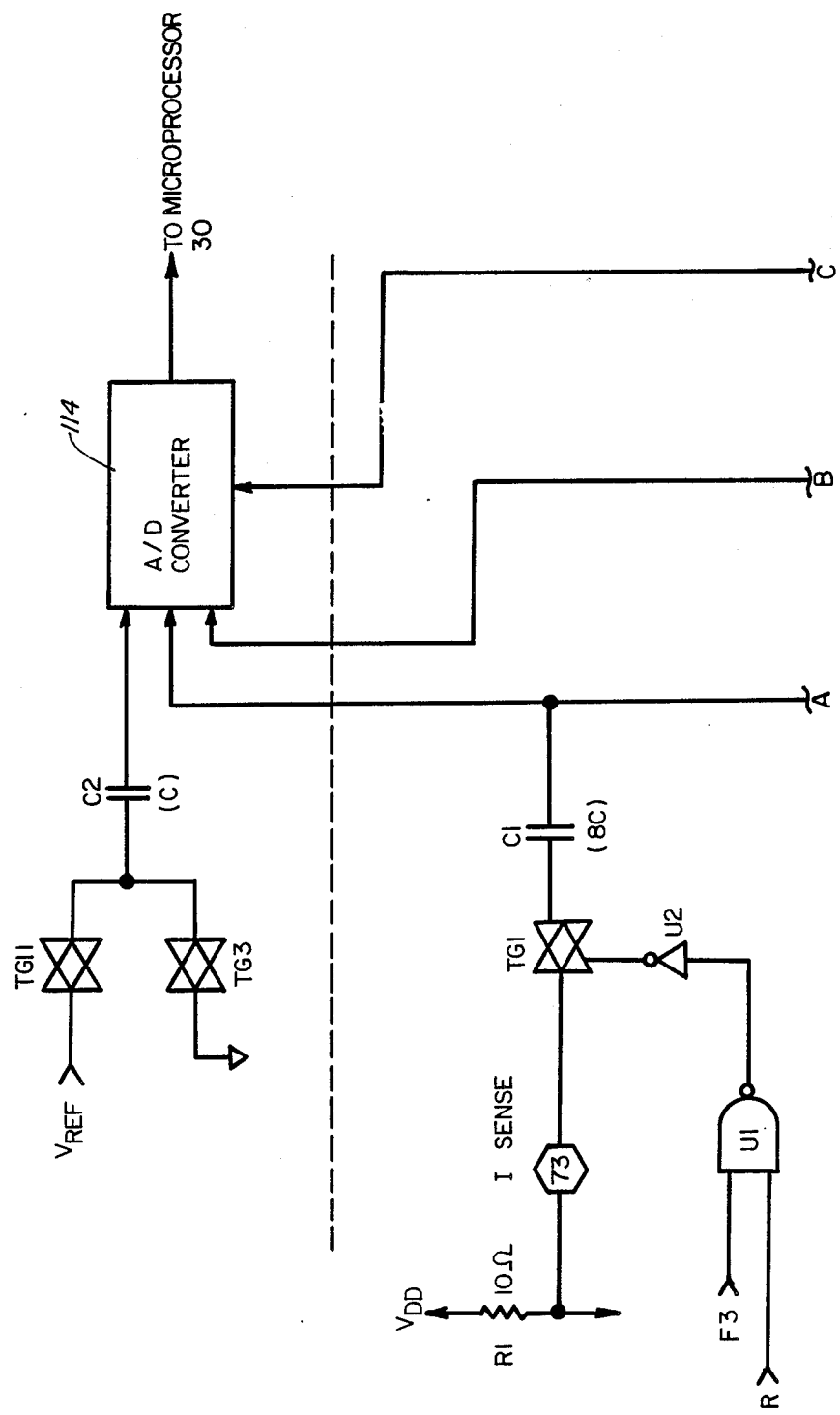
FIGS. 3a and 3b, when connected together, comprise a detailed schematic circuit diagrama of the internal measurement circuitry of the present invention.
Figure 3B:
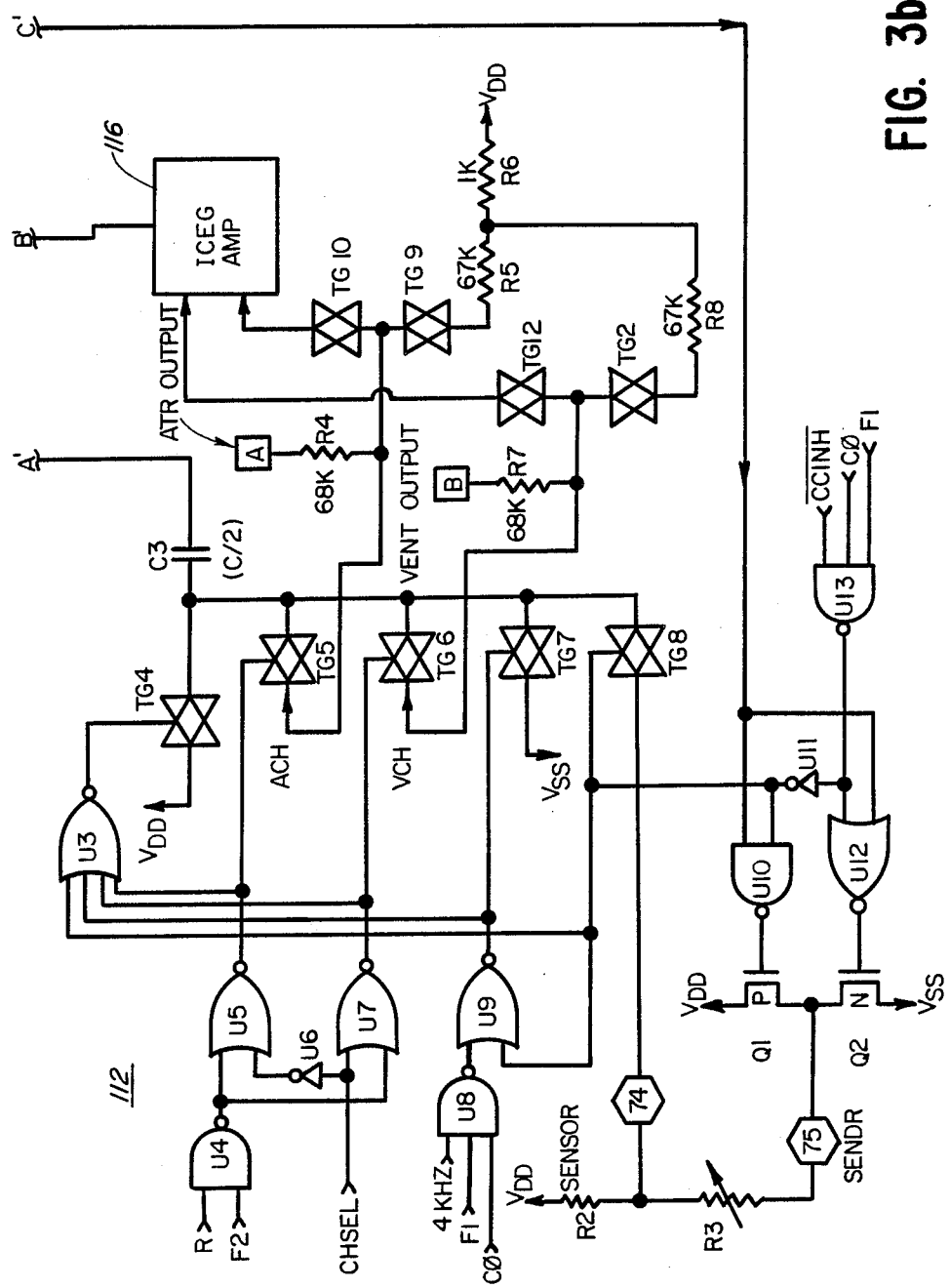

The detailed circuitry of the internal measuring circuit is illustrated in FIGS. 3a and 3b (connected together), and includes sampling measurement input circuitry 112, an analog-to-digital (A/D) convertor 114 and ICEG amplifiers 116. The inputs to the A/D convertor is either from the ICEG amplifiers 116 or from the measurement sampling input circuitry 112. The measurement input circuitry 112 includes a sensor element resistor R2 and a trimmed resistor R3 for determining battery terminal voltage measurements and battery sensor measurement. The junction of the resistors R2 and R3 is the net input voltage which is fed through a transmission gate TG 8 to an input capacitor C3. The other side of the capacitor C3 is fed into the A/D convertor 114 to generate an 8-bit serial data output when the proper commands are made by the microprocessor 30. The measured results are not immediately telemetered out, but are retained in assigned locations in the dedicated RAM 32. At a later time, the measured result may be telemetered to the programmer/receiver unit 10 for visual displat. Similarly, since $V_{DD}$ and $V_{SS}$ are the battery terminals, the sequential turning on of TG4 followed by TG7 causes the battery terminal voltage to be fed into the A/D convertor 114 through capacitor C3.

The input signals for the pulse voltage measurements for the atrial chamber of the pacer is received on pad A designated "ATR Output" which is fed through an attenuation network consisting of resistors R4, R5, and R6. With the transmission gate TG5 being turned on, the pulse voltage is fed through the input capacitor C3 to the A/D convertor 114. Similarly, the input signal for the pulse voltage measurement for the ventricle chamber is received on the pad B designated as "VENT Output" which is sent through an attenuation network consisting of resistors R7, R8 and R6. With the transmission gate TG6 being turned on, then the pulse voltage measurement for the ventricle chamber is measured through the input capacitor C3 and the A/D convertor 114. In the measurement mode, the transmission gates TG4 and TG7 are turned off or open and the transmission gates TG2 and TG9 are closed or turned on.

With respect to the output pulse current measurement, the input signal for both the atrial and ventricle current measurement are passed through a sensor resistor R1 to generate current sensing pulses which are fed through a transmission gate TG1 to the input capacitor C1 and then to the A/D convertor 112. Since the resistor R1 is used in the measurement of the output pulse current, the accuracy of pulse current measurements will be no better than the precise value of the resistor R1. Rather than mechanically trimming this resistor to the precise value such as 10 ohms, the calibration measurements can be made, as previously discussed, so as to compensate effectively for the differences between the actual value of the resistor R1 and the desired precise value of 10 ohms.

Similarly, the precise value of the resistors R4 through R8 will determine the accuracy of the pulse voltage measurements. The calibration measurements and the correction factor computed therefrom will enable effective compensation between the difference in the actual values of the resistors R4, R5, R6, R7 and R8 and their desired precise values of 68 K ohms, 67 K ohms, 1 K ohms, 68 K ohms and 67 K ohms, respectively.

The sampling input circuit 112 includes offset correction which is obtained by feeding a reference voltage step of $V_{ref}$ through capacitor C2 by turning on transmission gate TG3 and then transmission gate TG11 during the time when the measurement is made either from the input capacitor C1 or capacitor C3. This offset correction is summed into the A/D convertor 114 as a separate input and made coincident with the pulse current measurement through the capacitor C1 or with the pulse voltage measurement through the capacitor C3. This permits the output of the A/D convertor 114 to operate over a full scale positive and negative output range.

From the foregoing detailed description, it can thus be seen that the present invention provides an improved cardiac pacer having means for calibrating internal measurements thereof by software trim. To this end, the pacer includes a RAM device with dedicated locations for storing programmed correction factors for the uncorrected measurement signals. A programmer/receiver unit includes a ROM device for storing an algorithm and a microprocessor for calculating corresponding measurement values for display from the uncorrected measurements and the correction factors.

While it has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out this invention, but that this invention include all embodiments falling within the scope of the appended claims.

What is claimed is:

1. A method of calibrating internal measurements obtained through plated resistors formed on an integrated circuit in an implanted cardiac pacer, comprising the steps of:
   measuring uncorrected values through plated resistors by an internal measurement circuit relative to at least one of battery conditions and pulses from a pacing circuit;
   obtaining correct values during the manufacturing process by a precise external instrument relative to at least one of the battery conditions and the pulses from the pacing circuit;
   comparing the uncorrected values with the correct values in order to provide correction factors;
   storing the correction factors for the uncorrected values in a memory device located within the implant;
   telemetering uncorrected values and the correction factors to an external programmer/receiver;
   computing corrected values in the external programmer/receiver from the telemetered uncorrected values and the telemetered correction factors in order to compensate effectively for the difference between the actual values of the resistors and the precise values of the resistors, so that the necessity of mechanically trimming the resistors to be of precise values after manufacturing is eliminated.

2. A method as described in claim 1, including the step of displaying the corrected values in the external programmer/receiver.

3. A method as described in claim 1, including the step of connecting a dummy load representing the atrial heart chamber to the leads of a pacer during the steps of (a) measuring uncorrected values by an internal measurement circuit and (b) obtaining correct values by an external instrument.

4. A method as described in claim 3, in which the correction factors include a gain correction factor and an offset correction factor.

5. A method as described in claim 1, in which internal measurements are made of a maximum current output pulse and a minimum current output pulse and external measurements are made of an exact maximum current output pulse and an exact minimum output pulse.

6. A method as described in claim 5, in which the correction factors include a gain factor and an offset factor that is computed by comparing the differences between the external measurements and the internal measurements.

* * * * *